United States Patent
Neidlein et al.

(10) Patent No.: US 6,566,307 B1
(45) Date of Patent: May 20, 2003

(54) α,α'-SUBSTITUTED N-ALKYL-3-ALKENYLBENZOYL-PYRAZOL-DERIVATIVES

(75) Inventors: Ulf Neidlein, Mannheim (DE); Norbert Götz, Worms (DE); Ernst Baumann, Dudenhofen (DE); Wolfgang von Deyn, Neustadt (DE); Steffen Kudis, Mannheim (DE); Roland Götz, Neulussheim (DE); Klaus Langemann, Worms (DE); Guido Mayer, Neustadt (DE); Ulf Misslitz, Neustadt (DE); Matthias Witschel, Ludwigshafen (DE); Martina Otten, Ludwigshafen (DE); Karl-Otto Westphalen, Speyer (DE); Helmut Walter, Obrigheim (DE)

(73) Assignee: BASF Aktiengesellschaft, Ludwigshafen (DE)

(*) Notice: Subject to any disclaimer, the term of this patent is extended or adjusted under 35 U.S.C. 154(b) by 0 days.

(21) Appl. No.: 10/019,542
(22) PCT Filed: Jun. 23, 2000
(86) PCT No.: PCT/EP00/05857
§ 371 (c)(1), (2), (4) Date: Jan. 3, 2002
(87) PCT Pub. No.: WO01/04095
PCT Pub. Date: Jan. 18, 2001

(30) Foreign Application Priority Data
Jul. 9, 1999 (DE) .......................... 199 31 881

(51) Int. Cl.[7] .......................... A01N 43/56; C07D 23/20
(52) U.S. Cl. .......................... 504/282; 548/369.4
(58) Field of Search .......................... 548/369.4; 504/282

(56) References Cited

U.S. PATENT DOCUMENTS

| | | |
|---|---|---|
| 4,948,887 A | 8/1990 | Baba et al. |
| 5,807,806 A | 9/1998 | Tanaka et al. |
| 6,143,696 A | 11/2000 | Baumann et al. |

FOREIGN PATENT DOCUMENTS

| | | |
|---|---|---|
| EP | 282 944 | 9/1988 |
| EP | 990 649 | 4/2000 |
| WO | 98/42677 | 10/1998 |
| WO | 98/45273 | 10/1998 |
| WO | 98/52926 | 11/1998 |

OTHER PUBLICATIONS

Derwent 98/447454/47—WO 9845273–A1.

Primary Examiner—Robert W. Ramsuer
(74) Attorney, Agent, or Firm—Keil & Weinkauf

(57) ABSTRACT

Pyrazoles of the formula I

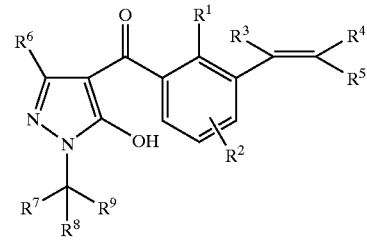

where:

$R^1$ is hydrogen, nitro, halogen, cyano, thiocyanato or an aliphatic radical;

$R^2$ is a substituted sulfur, nitrogen or phosphorus atom;

$R^3$ is hydrogen, halogen or an aliphatic radical;

$R^4$, $R^5$ are hydrogen, nitro, halogen, cyano, thiocyanato, or an aliphatic radical;

$R^6$ is hydrogen, halogen, $C_1$–$C_6$-alkyl, $C_1$–$C_6$-alkoxy, $C_3$–$C_8$-cycloalkyl;

$R^7$, $R^8$, $R^9$ are hydrogen, $C_1$–$C_6$-alkyl, but at most one of the radicals $R^7$, $R^8$ and $R^9$ is hydrogen;

and their tautomers and agriculturally useful salts are described.

Moreover, the invention relates to processes for preparing compounds of the formula I, to compositions comprising them and to the use of the compounds of the formula I and of the compositions comprising them for controlling harmful plants.

16 Claims, No Drawings

α,α'-SUBSTITUTED N-ALKYL-3-ALKENYLBENZOYL-PYRAZOL-DERIVATIVES

This application is a 371 of PCT/EP00/05857 filed Jun. 23, 2000.

The present invention relates to α,α'-substituted N-alkyl-3-alkenylbenzoylpyrazole derivatives of the formula I

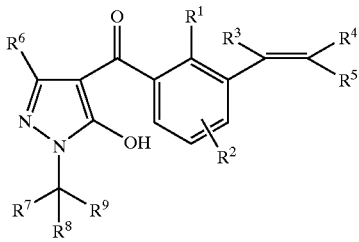

where:
- $R^1$ is hydrogen, nitro, halogen, cyano, thiocyanato, $C_1$–$C_6$-alkyl, $C_1$–$C_6$-alkoxy, $C_1$–$C_6$-haloalkyl, $C_1$–$C_6$-alkylthio, $C_2$–$C_6$-alkenyl, $C_2$–$C_6$-alkynyl;
- $R^2$ is —$S(O)_nR^{10}$, —$SO_2OR^{11}$, —$SO_2NR^{11}R^{12}$, —$NR^{12}SO_2R^{13}$, —$NR^{12}COR^{13}$, —$PO(OR^{14})(OR^{15})$;
- $R^3$ is hydrogen, halogen, $C_1$–$C_6$-alkyl, $C_1$–$C_6$-haloalkyl, $C_1$–$C_6$-alkoxy, $C_2$–$C_6$-alkenyl or $C_2$–$C_6$-alkynyl;
- $R^4$, $R^5$ are hydrogen, nitro, halogen, cyano, thiocyanato, $C_1$–$C_6$-alkyl, $C_1$–$C_6$-haloalkyl, $C_3$–$C_6$-cycloalkyl, $C_2$–$C_6$-alkenyl, $C_4$–$C_6$-cycloalkenyl, $C_2$–$C_6$-alkynyl, $C_1$–$C_6$-alkylthio, $C_1$–$C_6$-haloalkoxy, —$COR^{14}$, —$CO_2R^{14}$, —$COSR^{14}$, —$CONR^{14}R^{15}$, —$C(R^{16})$=$NR^{17}$, —$PO(OR^{14})(OR^{15})$, $C_1$–$C_4$-alkyl, which carries a radical from the following group: —$COR^{14}$, —$CO_2R^{14}$, —$COSR^{14}$, —$CONR^{14}R^{15}$ or —$C(R^{16})$=$NR^{17}$; heterocyclyl, heterocyclyl-$C_1$–$C_4$-alkyl, phenyl, phenyl-$C_1$–$C_4$-alkyl, hetaryl or hetaryl-$C_1$–$C_4$-alkyl, where the six last-mentioned radicals may be substituted;

or
- $R^4$ and $R^5$ together form a $C_2$–$C_6$-alkanediyl chain which may be mono- to tetrasubstituted by $C_1$–$C_4$-alkyl and/or may be interrupted by oxygen or sulfur or an unsubstituted or $C_1$–$C_4$-alkyl-substituted nitrogen;
- $R^6$ is hydrogen, halogen, $C_1$–$C_6$-alkyl, $C_1$–$C_6$-alkoxy, $C_3$–$C_8$-cycloalkyl;
- $R^7$, $R^8$, $R^9$ are hydrogen, $C_1$–$C_6$-alkyl, where the alkyl group may be unsubstituted or mono- or polysubstituted by halogen or cyano and the radicals $R^7$, $R^8$ and $R^9$ are in each case identical or different, but at most one of the radicals from the group $R^7$, $R^8$ and $R^9$ is hydrogen;
- n is 0, 1 or 2;
- $R^{10}$ is $C_1$–$C_6$-alkyl, $C_1$–$C_6$-haloalkyl, $C_1$–$C_6$-alkoxy-$C_2$–$C_6$-alkyl, $C_3$–$C_6$-alkenyl or $C_3$–$C_6$-alkynyl;
- $R^{11}$ is hydrogen, $C_1$–$C_6$-alkyl, $C_1$–$C_6$-haloalkyl, $C_1$–$C_6$-alkoxy-$C_2$–$C_6$-alkyl, $C_3$–$C_6$-alkenyl or $C_3$–$C_6$-alkynyl;
- $R^{12}$ is hydrogen or $C_1$–$C_6$-alkyl;
- $R^{13}$ is $C_1$–$C_6$-alkyl or $C_1$–$C_6$-haloalkyl;
- $R^{14}$ is hydrogen, $C_1$–$C_6$-alkyl, $C_3$–$C_6$-cycloalkyl, $C_1$–$C_6$-haloalkyl, $C_3$–$C_6$-alkenyl, $C_3$–$C_6$-alkynyl, phenyl or benzyl, where the two last-mentioned radicals may be partially or fully halogenated and/or may carry one to three radicals from the following group: nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylcarbonyl or $C_1$–$C_4$-alkoxycarbonyl;
- $R^{15}$ is hydrogen, $C_1$–$C_6$-alkyl, $C_3$–$C_6$-alkenyl or $C_3$–$C_6$-alkynyl;

or
- $R^{14}$ and $R^{15}$ together form a $C_2$–$C_6$-alkanediyl chain which may be mono- to tetrasubstituted by $C_1$–$C_4$-alkyl and/or may be interrupted by oxygen or sulfur or an unsubstituted or $C_1$–$C_4$-alkyl-substituted nitrogen;
- $R^{16}$ is hydrogen, $C_1$–$C_6$-alkyl, $C_1$–$C_6$-haloalkyl, $C_1$–$C_6$-alkoxy, $C_1$–$C_6$-alkoxycarbonyl, $C_3$–$C_6$-cycloalkyl, $C_2$–$C_6$-alkenyl, $C_2$–$C_6$-alkynyl, phenyl or benzyl, where the two last-mentioned radicals may be partially or fully halogenated and/or may carry one to three radicals from the following group: nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylcarbonyl or $C_1$–$C_4$-alkoxycarbonyl;
- $R^{17}$ is $C_1$–$C_6$-alkyl, $C_1$–$C_6$-haloalkyl, $C_3$–$C_6$-cycloalkyl, $C_3$–$C_6$-alkenyl, $C_3$–$C_6$-alkynyl, $C_1$–$C_6$-alkoxy, $C_1$–$C_6$-haloalkoxy, $C_3$–$C_6$-cycloalkoxy, $C_3$–$C_6$-alkenyloxy, $C_3$–$C_6$-alkynyloxy, phenyl, benzyl or benzyloxy, where the three last-mentioned radicals may be partially or fully halogenated and/or may carry one to three radicals from the following group: nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylcarbonyl or $C_1$–$C_4$-alkoxycarbonyl;

and their tautomers and agriculturally useful salts.

Moreover, the invention relates to processes for preparing compounds of the formula I, to compositions comprising them and to the use of the compounds of the formula I and of the compositions comprising them in the agronomic field, in particular for controlling undesirable vegetation.

Herbicidally active compounds of the class of the benzoylpyrazoles are disclosed, for example, in EP-A 282 944; WO 98/42677; WO 98/45273; WO98/50366; WO 98/52926; WO 98/56766; U.S. Pat. No. 5,807,806.

However, the herbicidal properties of these compounds and their compatibility with crop plants are not entirely satisfactory.

It is an object of the present invention to provide novel compounds having improved properties which can be used as active compounds in crop protection, in particular as herbicides.

We have found that this object is achieved by the benzoylpyrazoles defined above, which are substituted in the 1-position of the pyrazole derivative by a branched alkyl group. This branched alkyl group is characterized by the substitutent —$CR^7R^8R^9$ on the pyrazole ring.

Furthermore, we have found highly effective compositions comprising the compounds I. Moreover, we have found processes for preparing these compositions and methods for controlling undesirable vegetation using the compounds I.

The present invention also provides stereoisomers of the compounds of the formula I. This includes both pure stereoisomers and mixtures thereof.

The compounds of the formula I contain a carbon-carbon double bond and are therefore present as E isomers or as z isomers or as E/Z isomer mixtures. Furthermore, the compounds of the formula I can contain further carbon or carbon-nitrogen double bonds. The invention provides both the pure geometric isomers and mixtures thereof.

Likewise, depending on the substitution pattern, the compounds of the formula I can contain one or more chiral centers, in which case they are present as enantiomers or diastereomer mixtures. The invention provides both the pure enantiomers or diastereomers and mixtures thereof.

The compounds of the formula I can also be present in the form of their tautomers or as tautomer mixtures. The tautomeric forms result in particular owing to the hydroxyl substituent at the pyrazole ring. Thus, the compounds can be referred to both as 5-hydroxypyrazoles and as 5-oxo-pyrazolinones.

The present invention also provides precursors which afford compounds I by chemical conversion or biological degradation. Such precursors of compounds I are, for example, esters or ether derivatives of functional hydroxyl groups.

The compounds of the formula I can also be present in the form of their agriculturally useful salts, the type of salt generally being immaterial. In general, the salts of those cations or the acid addition salts of those acids are suitable whose cations and anions, respectively, do not adversely affect the herbicidal action of the compounds I.

Suitable cations are, in particular, ions of the alkali metals, preferably lithium, sodium and potassium, of the alkaline earth metals, preferably calcium and magnesium, and of the transition metals, preferably manganese, copper, zinc and iron, and also ammonium, where, if desired, one to four hydrogen atoms may be replaced by $C_1$–$C_4$-alkyl or hydroxy-$C_1$–$C_4$-alkyl and/or one phenyl or benzyl, preferably diisopropylammonium, tetramethylammonium, tetrabutylammonium, trimethylbenzylammonium, furthermore phosphonium ions, sulfonium ions, preferably tri($C_1$–$C_4$-alkyl)-sulfonium and sulfoxonium ions, preferably tri($C_1$–$C_4$-alkyl)-sulfoxonium.

Anions of suitable acid addition salts are primarily chloride, bromide, fluoride, hydrogen sulfate, sulfate, dihydrogen phosphate, hydrogen phosphate, nitrate, bicarbonate, carbonate, hexafluorosilicate, hexafluorophosphate, benzoate and the anions of $C_1$–$C_4$-alkanoic acids, preferably formate, acetate, propionate and butyrate.

Essential for the invention for the purpose of the present invention are compounds of the formula I which are substituted by a branched alkyl group —$CR^7R^8R^9$ in the 1-position of the pyrazole ring. These are in particular those compounds I in which at most one of the radicals from the group consisting of $R^7$, $R^8$ and $R^9$ is hydrogen and the other two radicals are different from hydrogen (for example $R^7$=H and $R^8$≠H, $R^9$≠H).

The organic molecular moieties mentioned for the substituents $R^1$–$R^{17}$ are collective terms for individual enumerations of the individual group members. All hydrocarbon chains, i.e. all alkyl, haloalkyl, cycloalkyl, alkoxyalkyl, alkoxy, haloalkoxy, cycloalkoxy, alkylthio, alkylsulfonyl, haloalkylsulfonyl, alkylcarbonyl, haloalkylcarbonyl, alkoxycarbonyl, alkenyl, cycloalkenyl, alkynyl, alkenyloxy and alkynyloxy moieties can be straight-chain or branched. Unless indicated otherwise, halogenated substituents preferably carry one to five identical or different halogen atoms. The term halogen in each case denotes fluorine, chlorine, bromine or iodine.

Examples of other meanings are:

$C_2$–$C_4$-alkyl: ethyl, n-propyl, 1-methylethyl, butyl, 1-methylpropyl, 2-methylpropyl or 1,1-dimethylethyl;

$C_1$–$C_4$-alkyl, and the alkyl moieties of, for example, $C_1$–$C_4$-alkylcarbonyl, heterocyclyl-$C_1$–$C_4$-alkyl, phenyl-$C_1$–$C_4$-alkyl and hetaryl-$C_1$–$C_4$-alkyl: $C_2$–$C_4$-alkyl as mentioned above, and also methyl;

$C_2$–$C_6$-alkyl, and the alkyl moieties of, for example, $C_1$–$C_6$-alkoxy-$C_2$–$C_6$-alkyl: $C_2$–$C_4$-alkyl as mentioned above, and also pentyl 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl or 1-ethyl-3-methylpropyl;

$C_1$–$C_6$-alkyl, and the alkyl moieties of, for example, $C_1$–$C_6$-alkoxy-$C_1$–$C_6$-alkyl and $C_1$–$C_6$-alkylcarbonyl: $C_2$–$C_6$-alkyl as mentioned above, and also methyl;

$C_1$–$C_4$-haloalkyl: a $C_1$–$C_4$-alkyl radical as mentioned above which is partially or fully substituted by fluorine, chlorine, bromine and/or iodine, i.e., for example, chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl;

$C_1$–$C_6$-haloalkyl, and the haloalkyl moieties of $C_1$–$C_6$-haloalkylcarbonyl: $C_1$–$C_4$-haloalkyl as mentioned above, and also 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl or dodecafluorohexyl;

$C_1$–$C_4$-alkoxy, and the alkoxy moieties of $C_1$–$C_4$-alkoxycarbonyl: methoxy, ethoxy, propoxy, 1-methylethoxy, butoxy, 1-methylpropoxy, 2-methylpropoxy or 1,1-dimethylethoxy;

$C_1$–$C_6$-alkoxy, and the alkoxy moieties of $C_1$–$C_6$-alkoxy-$C_1$–$C_6$-alkyl, $C_1$–$C_6$-alkoxy-$C_2$–$C_6$-alkyl and $C_1$–$C_6$-alkoxycarbonyl: $C_1$–$C_4$-alkoxy as mentioned above, and also pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy;

$C_1$–$C_4$-haloalkoxy: a $C_1$–$C_4$-alkoxy radical as mentioned above which is partially or fully substituted by fluorine, chlorine, bromine and/or iodine, i.e., for example, fluoromethoxy, difluoromethoxy, trifluoromethoxy, chlorodifluoromethoxy, bromodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3- trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy or nonafluorobutoxy;

$C_1$–$C_6$-haloalkoxy: $C_1$–$C_4$-haloalkoxy as mentioned above, and also, for example, 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy or dodecafluorohexoxy;

$C_1$–$C_6$-alkylthio: for example, methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio;

$C_1$–$C_6$-alkylsulfonyl ($C_1$–$C_6$-alkyl-S(=O)$_2$—): for example methylsulfonyl, ethylsulfonyl, propylsulfonyl, 1-methylethylsulfonyl, butylsulfonyl, 1-methylpropylsulfonyl, 2-methylpropylsulfonyl or 1,1-dimethylethylsulfonyl, pentylsulfonyl, 1-methylbutylsulfonyl, 2-methylbutylsulfonyl, 3-methylbutylsulfonyl, 2,2-dimethylpropylsulfonyl, 1-ethylpropylsulfonyl, 1,1-dimethylpropylsulfonyl, 1,2-dimethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl 1-ethyl-1-methylpropylsulfonyl or 1-ethyl-2-methylpropylsulfonyl;

$C_1$–$C_6$-haloalkylsulfonyl: a $C_1$–$C_6$-alkylsulfonyl radical as mentioned above which is partially or fully substituted by fluorine, chlorine, bromine and/or iodine, i.e. fluoromethylsulfonyl, difluoromethylsulfonyl, trifcluoromethylsulfonyl, chlorodifluoromethylsulfonyl, bromodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2,2,2-trichloroethylsulfonyl, 2-chloro-2-fluoroethylsulfonyl, 2-chloro-2,2-difluoroethylsulfonyl, 2,2-dichloro-2-fluoroethylsulfonyl, pentafluoroethylsulfonyl, 2-fluoropropylsulfonyl, 3-fluoropropylsulfonyl, 2-chloropropylsulfonyl, 3-chloro propylsulfonyl, 2-bromopropylsulfonyl, 3-bromo propylsulfonyl, 2,2-difluoropropylsulfonyl, 2,3-difluoropropylsulfonyl, 2,3-dichloropropylsulfonyl, 3,3,3-trifluoropropylsulfonyl, 3,3,3-trichloropropylsulfonyl, 2,2,3,3,3-pentafluoropropylsulfonyl, heptafluoropropylsulfonyl, 1-(fluoromethyl)-2-fluoroethylsulfonyl, 1-(chloromethyl)-2-chloroethylsulfonyl, 1-(bromomethyl)-2-bromoethylsulfonyl, 4-fluorobutylsulfonyl, 4-chlorobutylsulfonyl, 4-bromobutylsulfonyl, Nonafluorobutylsulfonyl, 5-fluoropentylsulfonyl, 5-chloropentylsulfonyl, 5-bromopentylsulfonyl, 5-iodopentylsulfonyl, 6-fluorohexylsulfonyl, 6-bromohexylsulfonyl, 6-iodohexylsulfonyl or dodecafluorohexylsulfonyl;

$C_3$–$C_6$-alkenyl: prop-1-en-1-yl, prop-2-en-1-yl, 1-methylethenyl, buten-1-yl, buten-2-yl, buten-3-yl, 1-methylprop-3-en-1-yl, 2-methylprop-3-en-1-yl, 1-methylprop-2-en-1-yl, 2-methylprop-2-en-1-yl, penten-1-yl, penten-2-yl, penten-3-yl, penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, hex-1-en-1-yl, hex-2-en-1-yl, hex-3-en-1-yl, hex-4-en-1-yl, hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl or 1-ethyl-2-methylprop-2-en-1-yl;

$C_2$–$C_6$-alkenyl: $C_3$–$C_6$-alkenyl as mentioned above, and also ethenyl;

$C_3$–$C_6$-alkenyloxy: for example prop-1-en-1-yloxy, prop-2-en-1-yloxy, 1-methylethenyloxy, buten-1-yloxy, buten-2-yloxy, buten-3-yloxy, 1-methylprop-1-en-1-yloxy, 2-methylprop-1-en-1-yloxy, 1-methylprop-2-en-1-yloxy, 2-methylprop-2-en-1-yloxy, penten-1-yloxy, penten-2-yloxy, penten-3-yloxy, penten-4-yloxy, 1-methylbut-1-en-1-yloxy, 2-methylbut-1-en-1-yloxy, 3-methylbut-1-en-1-yloxy, 1-methylbut-2-en-1-yloxy, 2-methylbut-2-en-1-yloxy, 3-methylbut-2-en-1-yloxy, 1-methylbut-3-en-1-yloxy, 2-methylbut-3-en-1-yloxy, 3-methylbut-3-en-1-yloxy, 1,1-dimethylprop-2-en-1-yloxy, 1,2-dimethylprop-1-en-1-yloxy, 1,2-dimethylprop-2-en-1-yloxy, 1-ethylprop-1en-2-yloxy, 1-ethylprop-2-en-1-yloxy, hex-1-en-1-yloxy, hex-2-en-1-yloxy, hex-3-en-1-yloxy, hex-4-en-1-yloxy, hex-5-en-1-yloxy, 1-methylpent-1-en-1-yloxy, 2-methylpent-1-en-1-yloxy, 3-methylpent-1-en-1-yloxy, 4-methylpent-1-en-1-yloxy, 1-methylpent-2-en-1-yloxy, 2-methylpent-2-en-1-yloxy, 3-methylpent-2-en-1-yloxy, 4-methylpent-2-en-1-yloxy, 1-methylpent-3-en-1-yloxy, 2-methylpent-3-en-1-yloxy, 3-methylpent-3-en-1-yloxy, 4-methylpent-3-en-1-yloxy, 1-methylpent-4-en-1-yloxy, 2-methylpent-4-en-1-yloxy, 3-methylpent-4-en-1-yloxy, 4-methylpent-4-en- 1-yloxy, 1,1-dimethylbut-2-en-1-yloxy, 1,1-dimethylbut-3-en-1-yloxy, 1,2-dimethylbut-1-en-1-yloxy, 1,2-dimethylbut-2-en-1-yloxy, 1,2-dimethylbut-3-en-1-yloxy, 1,3-dimethylbut-1-en-1-yloxy, 1,3-dimethylbut-2-en-1-yloxy, 1,3-dimethylbut-3-en-1-yloxy, 2,2-dimethylbut-3-en-1-yloxy, 2,3-dimethylbut-1-en-1-yloxy, 2,3-dimethylbut-2-en-1-yloxy, 2,3-dimethylbut-3-en-1-yloxy, 3,3-dimethylbut-1-en-1-yloxy, 3,3-dimethylbut-2-en-1-yloxy, 1-ethylbut-1-en-1-yloxy, 1-ethylbut-2-en-1-yloxy, 1-ethylbut-3-en-1-yloxy, 2-ethylbut-1-en-1-yloxy, 2-ethylbut-2-en-1-yloxy, 2-ethylbut-3-en-1-yloxy, 1,1,2-trimethylprop-2-en-1-yloxy, 1-ethyl-1-methylprop-2-en-1-yloxy, 1-ethyl-2-methylprop-1-en-1-yloxy or 1-ethyl-2-methylprop-2-en-1-yloxy;

$C_3$–$C_6$-alkynyl: prop-1-yn-1-yl, prop-2-yn-1-yl, but-1-yn-1-yl, but-1-yn-3-yl, but-1-yn-4-yl, but-2-yn-1-yl, pent-1-yn-1-yl, pent-1-yn-3-yl, pent-1-yn-4-yl, pent-1-yn-5-yl, pent-2-yn-1-yl, pent-2-yn-4-yl, pent-2-yn-5-yl; 3-methylbut-1-yn-3-yl, 3-methylbut-1-yn-4-yl, hex-1-yn-1-yl, hex-1-yn-3-yl, hex-1-yn-4-yl, hex-1-yn-5-yl, hex-1-yn-6-yl, hex-2-yn-1-yl, hex-2-yn-4-yl, hex-2-yn-5-yl, hex-2-yn-6-yl, hex-3-yn-1-yl, hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl;

$C_2$–$C_6$-alkynyl: $C_3$–$C_6$-alkynyl as mentioned above, and also ethynyl:

$C_3$–$C_6$-alkynyloxy: for example prop-1-yn-1-yloxy, prop-2-yn-1-yloxy, but-1-yn-1-yloxy, but-1-yn-3-yloxy, but-1-yn-4-yloxy, but-2-yn-1-yloxy, pent-1-yn-1-yloxy, pent-1-yn-3-yloxy, pent-1-yn-4-yloxy, pent-1-yn-5-yloxy, pent-2-yn-1-yloxy, pent-2-yn-4-yloxy, pent-2-yn-5-yloxy, 3-methylbut-1-yn-3-yloxy, 3-methylbut-1-yn-4-yloxy, hex-1-yn-1-yloxy, hex-1-yn-3-yloxy, hex-1-yn-4-yloxy, hex-1-yn-5-yloxy, hex-1-yn-6-yloxy, hex-2-yn-1-yloxy, hex-2-yn-4-yloxy, hex-2-yn-5-yloxy, hex-2-yn-6-yloxy, hex-3-yn-1-yloxy, hex-3-yn-2-yloxy, 3-methylpent-1-yn-1-yloxy, 3-methylpent-1-yn-3-yloxy, 3-methylpent-1-yn-4-yloxy, 3-methylpent-1-yn-5-yloxy, 4-methylpent-1-yn-1-yloxy, 4-methylpent-2-yn-4-yloxy or 4-methylpent-2-yn-5-yloxy;

$C_3$–$C_6$-cycloalkyl: cyclopropyl, cyclobutyl, cycl or cyclohexyl;

$C_3$–$C_6$-cycloalkoxy: cyclopropoxy, cyclobutoxy, cyclopentoxy or cyclohexoxy;

$C_3$–$C_6$-cycloalkenyl: cyclopropen-1-yl, cyclobuten-3-yl, cyclopenten-1-yl, cyclopenten-3-yl, cyclohexen-1-yl, cyclohexen-3-yl or cyclohexen-4-yl;

heterocyclyl, and the heterocyclyl radicals in heterocyclyloxy and heterocyclyl-$C_1$–$C_4$-alkyl: three- to seven-membered saturated or partially unsaturated mono- or polycyclic heterocycles containing one to three hetero atoms selected from a group consisting of oxygen, nitrogen and sulfur, such as oxiranyl, 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofuran-2-yl, 2,3-dihydrofuran-3-yl, 2,3-dihydrofuran-4-yl, 2,3-dihydrofuran-5-yl, 2,5-dihydrofuran-2-yl, 2,5-dihydrofuran-3-yl, 2,3-dihydrothien-2-yl, 2,3-dihydrothien-3-yl, 2,3-dihydrothien-4-yl, 2,3-dihydrothien-5-yl, 2,5-dihydrothien-2-yl, 2,5-dihydrothien-3-yl, 2,3-dihydropyrrol-2-yl, 2,3-dihydropyrrol-3-yl, 2,3-dihydropyrrol-4-yl, 2,3-dihydropyrrol-5-yl, 2,5-dihydropyrrol-2-yl, 2,5-dihydropyrrol-3-yl, 2,3-dihydroisoxazol-3-yl, 2,3-dihydroisoxazol-4-yl, 2,3-dihydroisoxazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroisoxazol-5-yl, 2,3-dihydroisothiazol-3-yl, 2,3-dihydroisothiazol-4-yl, 2,3-dihydroisothiazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydropyrazol-3-yl, 2,3-dihydropyrazol-4-yl, 2,3-dihydropyrazol-5-yl, 4,5-dihydropyrazol-3-yl, 4,5-dihydropyrazol-4-yl, 4,5-dihydropyrazol-5-yl, 2,5-dihydropyrazol-3-yl, 2,5-dihydropyrazol-4-yl, 2,5-dihydropyrazol-5-yl, 2,3-dihydroxazol-2-yl, 2,3-dihydroxazol-4-yl, 2,3-dihydroxazol-5-yl, 4,5-dihydroxazol-2-yl, 4,5-dihydroxazol-4-yl, 4,5-dihydroxazol-5-yl, 2,5-dihydroxazol-2-yl, 2,5-dihydroxazol-4-yl, 2,5-dihydroxazol-5-yl, 2,3-dihydrothiazol-2-yl, 2,3-dihydrothiazol-4-yl, 2,3-dihydrothiazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydroimidazol-2-yl, 2,3-dihydroimidazol-4-yl, 2,3-dihydroimidazol-5-yl, 4,5-dihydroimidazol-2-yl, 4,5-dihydroimidazol-4-yl, 4,5-dihydroimidazol-5-yl, 2,5-dihydroimidazol-2-yl, 2,5-dihydroimidazol-4-yl, 2,5-dihydroimidazol-5-yl, 2-morpholinyl, 3-morpholinyl, 2-piperidinyl, 3-piperidinyl, 4-piperidinyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl, 1,2,4-tetrahydrotriazin-3-yl, 1,3-dihydroxazin-2-yl, 2-tetrahydropyranyl, 3-tetrahydropyranyl, 4-tetrahydropyranyl, 2-tetrahydrothiopyranyl, 3-tetrahydrothiopyranyl, 4-tetrahydrothiopyranyl, 1,3-dioxolan-2-yl, 1,3-dioxolan-4-yl, 1,3-dithiolan-2-yl, 1,3-dithiolan-4-yl, 1,3-dioxan-2-yl, 1,3-dioxan-4-yl, 1,3-dioxan-5-yl, 1,3-dithian-2-yl, 1,3-dithian-4-yl, 1,3-dithian-5-yl, 3,4,5,6-tetrahydropyridin-2-yl, 4H-1,3-thiazin-2-yl, 4H-3,1-benzothiazin-2-yl, 1,1-dioxo-2,3,4,5-tetrahydrothien-2-yl, 2H-1,4-benzothiazin-3-yl, 2H-1,4-benzoxazin-3-yl or 1,3-dihydroxazin-2-yl;

hetaryl, and the heteraryl radicals in hetaryloxy and hetaryl-$C_1$–$C_4$-alkyl: aromatic mono- or polycylclic radicals which, in addition to carbon ring members, may additionally contain one to four nitrogen atoms or one to three nitrogen atoms and one oxygen or one sulfur atom or one oxygen or one sulfur atom, for example, 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2pyrazinyl, 1,3,5-triazin-2-yl, 1,2,4-triazin-3-yl, 1,2,4,5-tetrazin-3-yl, and the corresponding benzo-fused derivatives;

$C_2$–$C_6$-alkanediyl: for example ethane-1,2-diyl, propane-1,3-diyl, butane-1,4-diyl, pentane-1,5-diyl or hexane-1,6-diyl;

All of the abovementioned phenyl, hetaryl and heterocyclyl rings can be substituted or unsubstituted. They are preferably unsubstituted. Substituted rings carry one to three halogen atoms and/or one or two radicals from the following group: nitro, cyano, $C_1$–$C_6$-alkyl, halo-$C_1$–$C_6$-alkyl, $C_1$–$C_6$-alkoxy, halo-$C_1$–$C_6$-alkoxy or $C_1$–$C_6$-alkoxycarbonyl, such as, for example, methyl, trifluoromethyl, methoxy, trifluoromethoxy or methoxycarbonyl.

Precursors of compounds I are, for example, ester or ether derivatives of functional hydroxyl groups. In this context, they are to be understood as meaning, in particular, those compounds of the formula I in which the hydroxyl group on the pyrazole ring is replaced by the following radicals: $C_1$–$C_6$-alkoxy, $C_3$–$C_6$-alkenyloxy, $C_1$–$C_6$-alkylsulfonyloxy, $C_1$–$C_6$-alkylcarbonyloxy, phenoxy-, phenyl-$C_1$–$C_4$-alkoxy, phenylcarbonyl-$C_1$–$C_4$-alkoxy, phenylsulfonyloxy, where the phenyl radical of the four lastmentioned substitutents may be partially or fully halogenated and/or may carry one to three of the following groups: nitro, cyano, $C_1$–$C_4$-alkyl, $C_1$–$C_4$-haloalkyl, $C_1$–$C_4$-alkoxy or $C_1$–$C_4$-haloalkoxy.

With respect to the use of the compounds of the formula I according to the invention as herbicides, the variables preferably have the following meanings, in each case on their own or in combination with one another, and some substituents, which fall under the general terms mentioned under a) are listed by way of example below, under b):

1. $R^1$:
   a) $C_1$–$C_6$-alkyl, $C_1$–$C_6$-alkoxy, halogen
   b) methyl, methoxy, chlorine
2. $R^2$ is preferably in the para position to the pyrazolyl carbonyl group and is, in particular:
   a) $C_1$–$C_6$-alkylsulfonyl
   b) methylsulfonyl, ethylsulfonyl
3. $R^3$
   a) hydrogen, $C_1$–$C_6$-alkyl, $C_1$–$C_6$-alkoxy
   b) methyl, methoxy
4. $R^4$
   a) hydrogen, $C_1$–$C_6$-alkyl, $C_1$–$C_6$-alkoxy, cyano
   b) methyl, ethyl, isopropyl, methoxy, ethoxy, cyano,
5. $R^5$
   a) hydrogen, $C_1$–$C_6$-alkyl, heterocyclyl
   b) hydrogen, methyl, isoxazolyl, which may be substituted by methyl,
6. $R^7$
   a) hydrogen, $C_1$–$C_6$-alkyl
   b) hydrogen, methyl, ethyl
7. $R^8$
   a) $C_1$–$C_6$-alkyl
   b) methyl, isopropyl
8. $R^9$
   a) $C_1$–$C_6$-alkyl
   b) methyl, isopropyl Preferred embodiments are those which display at least one or more of the abovementioned features (see items 1.–8.).

Particular preference is given to compounds of the formula I which have the following combinations of the radicals $R^7$, $R^8$ and $R^9$:

a) $R^7$=hydrogen, $R^8$=$R^9$=$C_1$–$C_6$-alkyl b) $R^7$=$R^8$=$R^9$=$C_1$–$C_6$-alkyl According to the invention, the herbicidal action of the benzoylpyrazoles can be increased advantageously by substituting the $N^1$-position of the pyrazolyl ring by a branched $C_1$–$C_6$-alkyl group ($\alpha,\alpha'$-N-alkyl-substituted benzoylpyrazoles). In principle, this activity increase occurs with all benzoylpyrazoles which have essential moieties of the biophor shown in the Formula I which is responsible for the herbicidal action of this class of compounds. In this context, the benzoylpyrazole group is an essential structural element. The other substituents present in this system can essentially be any radicals. However, preference is given to those benzoylpyrazoles which contain one or more of the following biophoric structural elements: an alkenyl group in the 3-position of the phenyl ring; a $C_1$–$C_6$-alkylsulfonyl group in the 4-position of the phenyl ring; a halogen, $C_1$–$C_6$-alkyl- or $C_1$–$C_6$-alkoxy group in the 2-position of the phenyl ring; a hydroxyl or alkoxy group in the 5-position of the pyrazolyl ring.

In the context of the present invention, the following compounds of the formulae Ia1–Ia6 are preferred embodiments:

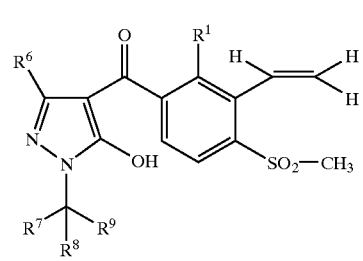

Ia1

TABLE 1

| No. | $R^1$ | $R^6$ | $R^7$ | $R^8$ | $R^9$ |
|---|---|---|---|---|---|
| Ia1.001 | O—CH$_3$ | H | CH$_3$ | CH$_3$ | H |
| Ia1.002 | Cl | H | CH$_3$ | CH$_3$ | H |
| Ia1.003 | CH$_3$ | H | CH$_3$ | CH$_3$ | H |
| Ia1.004 | O—CH$_3$ | CH$_3$ | CH$_3$ | CH$_3$ | H |
| Ia1.005 | Cl | CH$_3$ | CH$_3$ | CH$_3$ | H |
| Ia1.006 | CH$_3$ | CH$_3$ | CH$_3$ | CH$_3$ | H |
| Ia1.007 | O—CH$_3$ | CH$_3$ | CH$_3$ | CH$_3$ | CH$_3$ |
| Ia1.008 | Cl | CH$_3$ | CH$_3$ | CH$_3$ | CH$_3$ |
| Ia1.009 | CH$_3$ | CH$_3$ | CH$_3$ | CH$_3$ | CH$_3$ |
| Ia1.010 | O—CH$_3$ | H | CH$_3$ | H | i-C$_3$H$_7$ |
| Ia1.011 | Cl | H | CH$_3$ | H | i-C$_3$H$_7$ |
| Ia1.012 | CH$_3$ | H | CH$_3$ | H | i-C$_3$H$_7$ |
| Ia1.013 | O—CH$_3$ | H | H | i-C$_3$H$_7$ | i-C$_3$H$_7$ |
| Ia1.014 | Cl | H | H | i-C$_3$H$_7$ | i-C$_3$H$_7$ |
| Ia1.015 | CH$_3$ | H | H | i-C$_3$H$_7$ | i-C$_3$H$_7$ |
| Ia1.016 | O—CH$_3$ | H | C$_2$H$_5$ | CH$_3$ | CH$_3$ |
| Ia1.017 | Cl | H | C$_2$H$_5$ | CH$_3$ | CH$_3$ |
| Ia1.018 | CH$_3$ | H | C$_2$H$_5$ | CH$_3$ | CH$_3$ |

Preference is furthermore given to compounds Ia2, in particular the compounds Ia2.001–Ia2.018 which differ from the corresponding compounds Ia1.001–Ia1.018 in that $R^5$ in the formula I is methoxy:

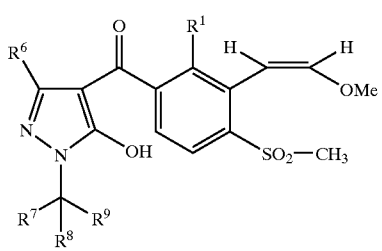

Ia2

Preference is furthermore given to compounds Ia3, in particular the compounds Ia3.001–Ia3.018 which differ from the corresponding compounds Ia1.001–Ia1.018 in that $R^5$ in the formula I is methyl:

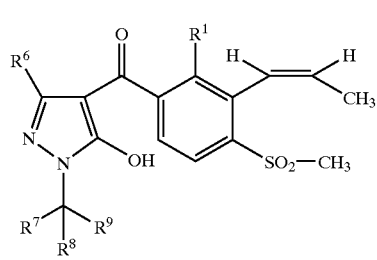

Ia3

Preference is furthermore given to compounds Ia4, in particular the compounds Ia4.001–Ia4.018 which differ from the corresponding compounds Ia1.001–Ia1.018 in that $R^5$ in the formula I is ethyl:

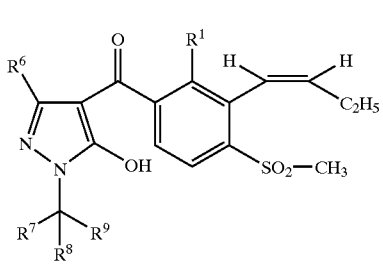

Ia4

Preference is furthermore given to compounds Ia5, in particular the compounds Ia5.001–Ia5.018 which differ from the corresponding compounds Ia1.001–Ia1.018 in that $R^5$ in the formula I is cyano:

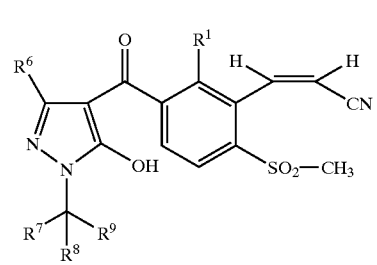

Ia5

Preference is furthermore given to compounds Ia6, in particular the compounds Ia6.001–Ia6.018 which differ from the corresponding compounds Ia1.001–Ia1.018 in that $R^5$ in the formula I is isopropyl:

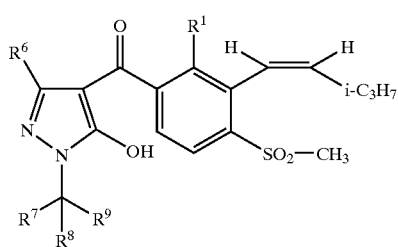

Ia6

The compounds of the formula I are essentially prepared by the processes described in WO 98/50366.

Particularly suitable is a process which comprises acylating a pyrazole of the formula II

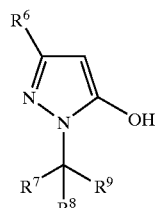

II with a carboxylic acid III or an activated derivative thereof

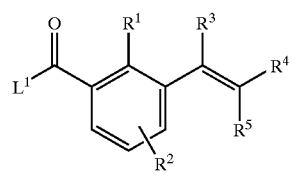

III where the variables $R^1$ to $R^5$ are as defined under claim 1 and $L^1$ is hydroxyl or a nucleophilically displaceable leaving group, and rearranging the acylation product in the presence or absence of a catalyst to the compounds I.

Compounds of the formula II are known from the literature or commercially available. Alternatively, compounds of the formula II can be prepared by the process described in DE 19910505.

Compounds of the formula III are disclosed, inter alia, in WO 98/50366 and the literature references cited therein.

In the reaction scheme below, a possible synthesis route for preparing compounds I starting from compounds A via the intermediates B, C and D is described in an exemplary manner for $R^1$=methoxy, $R^2$=methylsulfonyl, $R^3$=$R^4$=$R^5$= $R^6$=H, $R^7$=$R^8$CH$_3$, $R^9$=H (compound Ia1.01):

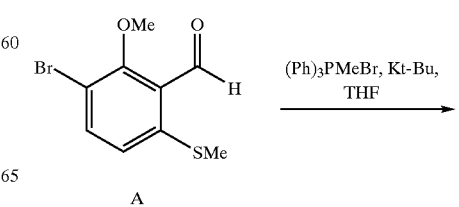

A

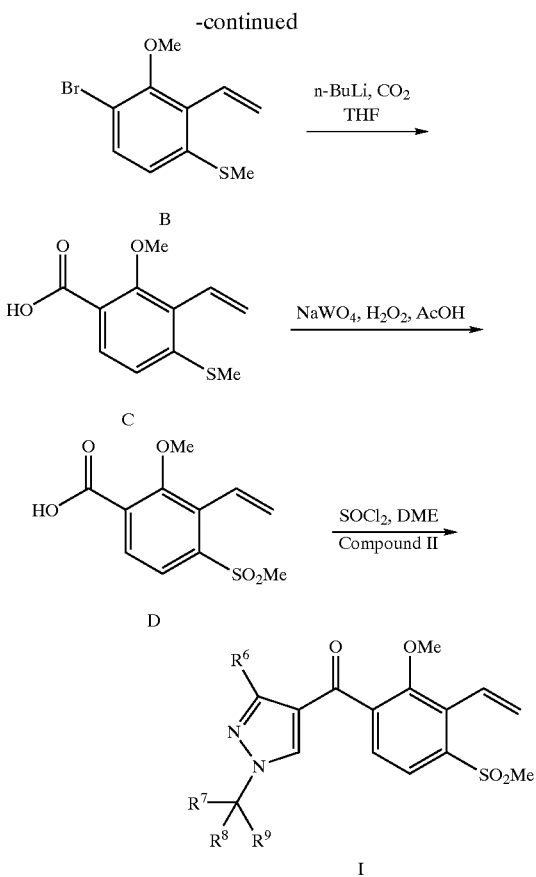

The compounds I can be present in the form of their agriculturally useful salts, the type of salt generally not being important. Suitable are usually the salts of those bases which do not adversely affect the herbicidal action of I.

Suitable basic salts are, in particular, those of the alkali metals, preferably the lithium, sodium and potassium salts, those of the alkaline earth metals, preferably calcium, magnesium and barium salts, and those of the transition metals, preferably manganese, copper, zinc and iron salts, ammonium salts, and ammonium salts which may carry one to four $C_1$–$C_4$-alkyl, or hydroxy-$C_1$–$C_4$-alkyl substituents, one phenyl or/benzyl substituent, preferably diethylammonium, diisopropylammonium, tetramethylammonium, tetrabutylammonium, trimelthylbenzylammonium, and trimethyl-(2-hydroxyethyl)-ammonium salts, the phosphonium salts, the sulfonium salts, preferably tri-($C_1$–$C_4$-) alkylsulfonium salts, and the sulfoxonium salts, preferably tri-($C_1$–$C_4$-)alkylsulfoxonium salts.

The compounds I and their agriculturally useful salts are suitable, both in the form of isomer mixtures and in the form of the pure isomers, as herbicides. The herbicidal compositions comprising compounds I control vegetation on non-crop areas very efficiently, especially at high rates of application. They act against broad-leaved weeds and harmful grasses in crops such as wheat, rice, maize, soya and cotton without causing any significant damage to the crop plants. This effect is mainly observed at low rates of application.

Depending on the application method used, the compounds I, or the compositions comprising them, can additionally be/employed in a further number of crop plants for eliminating undesirable plants. Examples of suitable crops are the following:

*Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum,* Malus spec., *Manihot esculenta, Medicago sativa,* Musa spec., *Nicotiana tabacum (N.rustica), Olea europaea, Oryza sativa, Phaseolus lunatus, Phaseolus vulgaris, Picea abies,* Pinus spec., *Pisum sativum, Prunus avium, Prunus persica, Pyrus communis, Ribes sylvestre, Ricinus communis, Saccharum officinarum, Secale cereale, Solanum tuberosum, Sorghum bicolor (s. vulgare), Theobroma cacao, Trifolium pratense, Triticum aestivum, Triticum durum, Vicia faba, Vitis vinifera* and *Zea mays.*

In addition, the compounds I may also be used in crops which tolerate the action of herbicides owing to breeding, including genetic engineering methods.

The herbicidal compositions or the active compounds can be applied pre- or post-emergence. If the active compounds are less well tolerated by certain crop plants, application techniques may be used in which the herbicidal compositions are sprayed, with the aid of the spraying equipment, in such a way that they come into contact as little as possible, if at all, with the leaves of the sensitive crop plants, while the active compounds reach the leaves of undesirable plants growing underneath, or the bare soil surface (post-directed, lay-by).

The compounds I, or the herbicidal compositions comprising them, can be used for example in the form of ready-to-spray aqueous solutions, powders, suspensions, also highly-concentrated aqueous, oily or other suspensions or dispersions, emulsions, oil dispersions, pastes, dusts, materials for broadcasting or granules, by means of spraying, atomizing, dusting, broadcasting or watering. The use forms depend on the intended aims; in any case, they should ensure a very fine distribution of the active compounds according to the invention.

Essentially, suitable inert auxiliaries include: mineral oil fractions of medium to high boiling point, such as kerosene and diesel oil, furthermore coal tar oils and oils of vegetable or animal origin, aliphatic, cyclic and aromatic hydrocarbons, e.g. paraffin, tetrahydronaphthalene, alkylated naphthalenes and their derivatives, alkylated benzenes and their derivatives, alcohols such as methanol, ethanol, propanol, butanol and cyclohexanol, ketones such as cyclohexanone, or strongly polar solvents, e.g. amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the compounds I, either as such or dissolved in an oil or solvent, can be homogenized in water by means of a wetting agent, tackifier, dispersant or emulsifier. Alternatively, it is possible to prepare concentrates comprising active substance, wetting agent, tackifier, dispersant or emulsifier and, if desired, solvent or oil, which are suitable for dilution with water.

Suitable surfactants are the alkali metal salts, alkaline earth metal salts and ammonium salts of aromatic sulfonic acids, e.g. ligno-, phenol-, naphthalene- and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene, or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for broadcasting and dusts can be prepared by mixing or grinding the active substances together with a solid carrier.

Granules, e.g. coated granules, impregnated granules and homogeneous granules, can be prepared by binding the active compounds to solid carriers. Solid carriers are mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate and ammonium nitrate, ureas, and products of vegetable origin, such as cereal meal, tree bark meal, wood meal and nutshell meal, cellulose powders, or other solid carriers.

The concentrations of the active compounds I in the ready-to-use preparations can be varied within wide ranges. In general, the formulations comprise from about 0.001 to 98% by weight, preferably 0.01 to 95% by weight, of at least one active compound. The active compounds are employed in a purity of from 90% to 100%, preferably 95% to 100% (according to the NMR spectrum).

The compounds I according to the invention can be formulated, for example, as follows:

I. 20 parts by weight of a compound I are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

II. 20 parts by weight of a compound I are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

III. 20 parts by weight of a compound I are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

IV. 20 parts by weight of a compound I are mixed thoroughly with 3 parts by weight of sodium diisobutylnaphthalene-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active compound.

V. 3 parts by weight of a compound I are mixed with 97 parts by weight of finely divided kaolin. This gives a dust which comprises 3% by weight of the active compound.

VI. 20 parts by weight of a compound I are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of a compound I is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII. 1 part by weight of a compound I is dissolved in a mixture composed of 80 parts by weight of cyclohexanone and 20 parts by weight of Wettol® EM 31 (nonionic emulsifier based on ethoxylated castor oil). This gives a stable emulsion concentrate.

To widen the activity spectrum and to achieve synergistic effects, the compounds I may be mixed with a large number of representatives of other herbicidal or growth-regulating active compound groups and then applied concomitantly. Suitable components for mixtures are, for example, 1,2,4-thiadiazoles, 1,3,4-thiadiazoles, amides, aminophosphoric acid and its derivatives, aminotriazoles, anilides, (het) aryloxyalkanoic acids and their derivatives, benzoic acid and its derivatives, benzothiadiazinones, 2-aroyl-1,3-cyclohexanediones, hetaryl aryl ketones, benzylisoxazolidinones, meta-$CF_3$-phenyl derivatives, carbamates, quinolinecarboxylic acid and its derivatives, chloroacetanilides, cyclohexane-1,3-dione derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

It may furthermore be advantageous to apply the compounds I, alone or else concomitantly in combination with other herbicides, in the form of a mixture with other crop protection agents, for example together with agents for controlling pests or phytopathogenic fungi or bacteria. Also of interest is the miscibility with mineral salt solutions, which are employed for treating nutritional and trace element deficiencies. Non-phytotoxic oils and oil concentrates may also be added.

The application rates of the active compound are from 0.001 to 3.0, preferably 0.01 to 1.0 kg/ha of active substance (a.s.), depending on the control target, the season, the target plants and the growth stage.

EXAMPLE 1

(5-Methoxy-1-cyclopropyl-1H-pyrazol-4-yl)(4-methylsulfonyl-2-methoxy-3-vinylphenyl) methanone a) 2-Methoxy-6-methylsulfanylbenzaldehyde

At 0° C. NaSMe (12.2 g, 0.18 mol) was added a little at a time to a solution of 2-chloro-6-methoxybenzaldehyde (20 g, 0.12 mol) in NMP (12.2 g, 0.18 mol). The solution was stirred at 0° C. for 3 h, and its color changed to black. The solution was subsequently stirred into approximately 2 l of ice-water and acidified to pH=3 using 10% strength HCl, and the precipitate was filtered off with suction.

Yield: 13.6 g (65%). $^1$H-NMR(270 MHz, CDCl$_3$): 2.4 (s, 3H); 3.9 (s, 3H); 6.8 (d, 1H); 6.95 (d, 1H); 7.42 (d, 1H); 10.6 (s, 1H).

b) 3-Bromo-2-methoxy-6-methylsulfanylbenzaldehyde

Bromine (28.8 g, 0.18 mol) (dissolved in dioxane (500 ml)) was added dropwise to a solution of 2-methoxy-6-methylsulfanylbenzaldehyde (22 g, 0.12 mol) in dioxane (500 ml), and the mixture was stirred at 50° C. for 6 h. The mixture was then concentrated, the residue was taken up in CH$_2$Cl$_2$ and the mixture was washed with water, dried over MgSO$_4$ and concentrated. The solid was recrystallized from diisopropyl ether.

Yield: 17.5 g (56%). $^1$H-NMR(270 MHz, CDCl$_3$): 2.40 (s, 3H); 3.90 (s, 3H); 6.72 (d, 1H); 6.85 (d, 1H); 7.42 (m, 1H); 10.6 (s, 1H).

c) 1-Bromo-2-methoxy-4-methylsulfanyl-3-vinylbenzene

At 0° C., potassium tert-butoxide (6.2 g, 55.4 mmol) was added to a solution of methyltriphenylphosphoniumbromide (19.7 g, 55.4 mmol) in THF (180 ml). At from −10 to −5° C., 3-bromo-2-methoxy-6-methylsulfanylbenzaldehyde (12 g, 46 mmol) dissolved in THF (180 ml) was then added, and the mixture was stirred overnight at RT for 7 h. The mixture was filtered, and the solution was admixed with H$_2$O (200 ml) and MTBE (200 ml) and then extracted with MTBE (200 ml). The combined organic phases were dried over MgSO$_4$ and concentrated. Chromatography (cyclohexane→cyclohexane/EtOAc 9:1) gave 1-bromo-2-methoxy-4-methylsulfanyl-3-vinylbenzene.

Yield: 4.67 g (39%). $^1$H-NMR(270 MHz, CDCl$_3$): 2.40 (s, 3H); 3.70 (s, 3H); 5.62 (dd, 1H); 5.90 (dd, 1H); 6.70–6.90 (m, 2H); 7.40 (s, 1H).

d) 2-Methoxy-4-methylsulfanyl-3-vinylbenzoic acid

At −100° C., n-BuLi (25 ml, 15% in n-hexane, 4.1 mmol) was added to a solution of 1-bromo-2-methoxy-4-methylsulfanyl-3-vinylbenzene (7 g, 31.3 mmol) in THF (300 ml), and the mixture was stirred at −100° C. for 20 min. At −100° C., CO$_2$ was then introduced (exothermic reaction up to −60° C.). At −80 to −90° C., the mixture was then stirred for another 1 h, and NaOH (100 ml) was added dropwise at −40° C. The solution was stirred into EtOAc (400 ml), and the mixture was extracted 3× with 5% strength NaOH and acidified to pH=1 using 10% strength HCl. The H$_2$O phase was extracted with EtOAc (300 ml), and the combined organic phases were dried over MgSO$_4$ and concentrated.

Yield: 6.8 g (98%). $^1$H-NMR(270 MHz, CDCl$_3$): 1.90 (s, 3H); 2.42 (s, 3H); 3.62 (s, 3H); 5.50–5.80 (m, 2H); 6.58–6.65 (m, 1H); 7.1 (d, 1H); 7.6 (d, 1H).

e) 4-Methylsulfonyl-2-methoxy-3-vinylbenzoic acid

NaWO$_4$ (cat.) was added to a solution of 2-methoxy-4-methylsulfanyl-3-vinylbenzoic acid, (6.8 g, 30 mmol) in AcOH (130 ml), H$_2$O$_2$ (8.6 ml, 76 mmol) was added dropwise and the mixture was stirred at room temperature for 5 h. The solution was concentrated, the residue was taken up in methylene chloride and the mixture was dried over magnesium sulfate and concentrated.

Yield: 4.8 g (61%). $^1$H-NMR(270 MHz, CDCl$_3$): 3.20 (s, 3H); 3.70 (s, 3H); 5.65–5.90 (m, 2H); 7.0–7.20 (m, 1H); 7.65–7.95 (m, 2H).

f) 5-Hydroxy-1-isopropyl-1H-pyrazol-4-yl)-(4-methylsulfonyl-2-methoxy-3-vinylphenyl) methanone SOCl$_2$ (1.2 g, 10 mmol) was added to a solution of 4-methylsulfonyl-2-methoxy-3-vinylbenzoic acid (1.6 g, 6 mmol) in toluene (60 ml) and the mixture was heated at reflux for 2 h. The mixture was then concentrated and the product was added to a solution of N-isopropylpyrazolone (6 mmol), K$_2$CO$_3$ (1.6 g, 11.6 mmol) in DME (30 ml) and the mixture was stirred at RT overnight. The mixture was subsequently heated at reflux for 2 h and concentrated and the residue was dissolved in H$_2$O. The H$_2$O phase was extracted 3× with CH$_2$Cl$_2$, and the combined organic phases were dried over MgSO$_4$ and concentrated.

EXAMPLE 2

In the manner as described in Example 1, it is possible to obtain the following compounds:

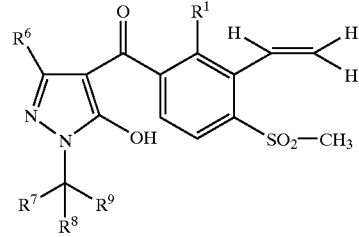

Ia1

| Ex. No. | R$^1$ | R$^6$ | R$^7$ | R$^8$ | R$^9$ | Mp. |
|---|---|---|---|---|---|---|
| 2.01 | O—CH$_3$ | H | CH$_3$ | CH$_3$ | H | 57–60° C. |
| 2.02 | Cl | H | CH$_3$ | CH$_3$ | H | |
| 2.03 | CH$_3$ | H | CH$_3$ | CH$_3$ | H | 134–135° C. |
| 2.04 | O—CH$_3$ | CH$_3$ | CH$_3$ | CH$_3$ | H | |
| 2.05 | Cl | CH$_3$ | CH$_3$ | CH$_3$ | H | |
| 2.06 | CH$_3$ | CH$_3$ | CH$_3$ | CH$_3$ | H | |
| 2.07 | O—CH$_3$ | CH$_3$ | CH$_3$ | CH$_3$ | CH$_3$ | |
| 2.08 | Cl | CH$_3$ | CH$_3$ | CH$_3$ | CH$_3$ | |
| 2.09 | CH$_3$ | CH$_3$ | CH$_3$ | CH$_3$ | CH$_3$ | |
| 2.10 | O—CH$_3$ | H | CH$_3$ | H | i-C$_3$H$_7$ | |
| 2.11 | Cl | H | CH$_3$ | H | i-C$_3$H$_7$ | |
| 2.12 | CH$_3$ | H | CH$_3$ | H | i-C$_3$H$_7$ | |
| 2.13 | O—CH$_3$ | H | H | i-C$_3$H$_7$ | i-C$_3$H$_7$ | |
| 2.14 | Cl | H | H | i-C$_3$H$_7$ | i-C$_3$H$_7$ | |
| 2.15 | CH$_3$ | H | H | i-C$_3$H$_7$ | i-C$_3$H$_7$ | |
| 2.16 | O—CH$_3$ | H | C$_2$H$_5$ | CH$_3$ | CH$_3$ | |
| 2.17 | Cl | H | C$_2$H$_5$ | CH$_3$ | CH$_3$ | |
| 2.18 | CH$_3$ | H | C$_2$H$_5$ | CH$_3$ | CH$_3$ | |
| 2.19 | OCH$_3$ | H | CH$_3$ | CH$_3$ | CH$_3$ | 57–60° C. |
| 2.20 | CH$_3$ | H | CH$_3$ | CH$_3$ | CH$_3$ | 122–124° C. |
| 2.21 | OC$_2$H$_5$ | H | CH$_3$ | CH$_3$ | H | 123–124° C. |
| 2.22 | OC$_2$H$_5$ | H | CH$_3$ | CH$_3$ | CH$_3$ | 106–108° C. |
| 2.23 | Cl | H | CH$_3$ | CH$_3$ | CH$_3$ | 117–125° C. |

EXAMPLE 3

In the same manner as described in Example 1, it is possible to obtain the following compounds:

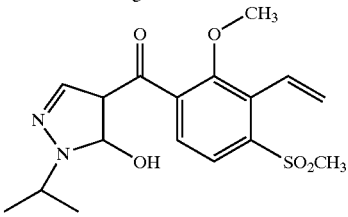
Ia3

| Ex. No. | $R^1$ | $R^6$ | $R^7$ | $R^8$ | $R^9$ | m.p. |
|---|---|---|---|---|---|---|
| 3.1[1)] | Cl | H | H | $CH_3$ | $CH_3$ | 44–54° C. |
| 3.2[1)] | $CH_3$ | H | H | $CH_3$ | $CH_3$ | 58–68° C. |
| 3.3[1)] | $CH_3$ | H | $CH_3$ | $CH_3$ | $CH_3$ | 63–74° C. |
| 3.4[2)] | Cl | H | $CH_3$ | $CH_3$ | $CH_3$ | 172–174° C. |

[1)] $R^5 = CH_3$
[2)] $R^5$ = 5-methylisoxazol-3-yl

EXAMPLE 4

The herbicidal activity of the compounds of the formula I was shown by greenhouse experiments:

The culture containers used are plastic pots containing loamy sand with approximately 3.0% of humus as the substrate. The seeds of the test plants are sown separately for each species.

For the pre-emergence treatment, the active compounds, which have been suspended or emulsified in water, were applied directly after sowing by means of finely distributing nozzles. The containers were irrigated gently to promote germination and growth and subsequently covered with transparent plastic hoods until the plants have rooted. This cover causes uniform germination of the test plants, unless this was adversely affected by the active compounds.

For the post-emergence treatment, the test plants were first grown to a height of 3 to 15 cm, depending on the plant form, and only then treated with the active compounds which have been suspended or emulsified in water. The test plants were for this purpose either sown directly and grown in the same containers, or they were first grown separately as seedlings and transplanted into the test containers a few days prior to treatment. The application rate for the post-emergence treatment was 0.25, 0.125 or 0.0625 kg of active substance (a.s.)/ha.

Depending on the species, the plants were kept at 10–25° C. or 20–35° C. The test period extended over 2 to 4 weeks. During this time, the plants are tended, and their response to the individual treatments was evaluated.

The evaluation was carried out using a scale from 0 to 100. 100 means no emergence of the plants, or complete destruction of at least the aerial parts and 0 means no damage, or normal course of growth.

The plants used in the greenhouse experiments were composed of the following species:

| Code | Common name |
|---|---|
| AMARE | pigweed |
| CHEAL | lambsquarter |
| ECHCG | barnyardgrass |
| POLPE | ladysthumb |
| SETVI | green foxtail |
| SINAL | white mustard |
| SOLNI | black nightshade |

TABLE 1

Herbicidal activity when used by the post-emergence method in a greenhouse

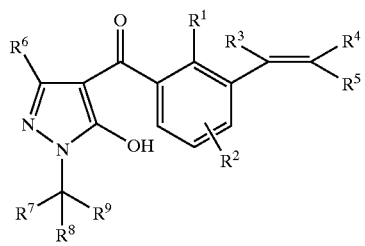

| | Application rate (kg of a.s./ha) | |
|---|---|---|
| Test plants | 0.125 | 0.0625 |
| ECHCG | 95 | 95 |
| SETVI | 95 | 95 |
| CHEAL | 100 | 100 |
| POLPE | 100 | 100 |
| SINAL | 98 | 98 |

We claim:
1. A pyrazole of the formula I

I where:
$R^1$ is hydrogen, nitro, halogen, cyano, thiocyanato, $C_1$–$C_6$-alkyl, $C_1$–$C_6$-alkoxy, $C_1$–$C_6$-haloalkyl, $C_1$–$C_6$-alkylthio, $C_2$–$C_6$-alkenyl, $C_2$–$C_6$-alkynyl;
$R^2$ is —S(O)$_n$$R^{10}$, —SO$_2$OR$^{11}$, —SO$_2$NR$^{11}$R$^{12}$, —NR$^{12}$SO$_2$R$^{13}$, —NR$^{12}$COR$^{13}$, —PO(OR$^{14}$)(OR$^{15}$);
$R^3$ is hydrogen, halogen, $C_1$–$C_6$-alkyl, $C_1$–$C_6$-haloalkyl, $C_1$–$C_6$-alkoxy, $C_2$–$C_6$-alkenyl or $C_2$–$C_6$-alkynyl;
$R^4$, $R^5$ are hydrogen, nitro, halogen, cyano, thiocyanato, $C_1$–$C_6$-alkyl, $C_1$–$C_6$-haloalkyl, $C_3$–$C_6$-cycloalkyl, $C_2$–$C_6$-alkenyl, $C_4$–$C_6$-cycloalkenyl, $C_2$–$C_6$-alkynyl, $C_1$–$C_6$-alkylthio, $C_1$–$C_6$-haloalkoxyl, —COR$^{14}$, —CO$_2$R$^{14}$, —COSR$^{14}$, —CONR$^{14}$R$^{15}$, —C(R$^{16}$)=NR$^{17}$, —PO(OR$^{14}$)(OR$^{15}$), $C_1$–$C_4$-alkyl, which carries a radical from the following group: —COR$^{14}$, —CO$_2$R$^{14}$, —COSR$^{14}$, —CONR$^{14}$R$^{15}$ or —C(R$^{16}$)=NR$^{17}$; heterocyclyl, heterocyclyl-$C_1$–$C_4$-alkyl, phenyl, phenyl-$C_1$–$C_4$-alkyl, hetaryl or hetaryl-$C_1$–$C_4$-alkyl, where the six last-mentioned radicals may be substituted;

or

R⁴ and R⁵ together form a $C_2$–$C_6$-alkanediyl chain which may be mono- to tetrasubstituted by $C_1$–$C_4$-alkyl and/or may be interrupted by oxygen or sulfur or an unsubstituted or $C_1$–$C_4$-alkyl-substituted nitrogen;

$R^6$ is hydrogen, halogen, $C_1$–$C_6$-alkyl, $C_1$–$C_6$-alkoxy, $C_3$–$C_8$-cycloalkyl;

$R^7$, $R_8$, $R^9$ are hydrogen, $C_1$–$C_6$-alkyl, where the alkyl group may be unsubstituted or mono- or polysubstituted by halogen or cyano and the radicals $R^7$, $R^8$ and $R^9$ are in each case identical or different, but at most one of the radicals of the group $R^7$, $R^8$ and $R^9$ is hydrogen;

n is 0, 1 or 2;

$R^{10}$ is $C_1$–$C_6$-alkyl, $C_1$–$C_6$-haloalkyl, $C_1$–$C_6$-alkoxy-$C_2$–$C_6$-alkyl, $C_3$–$C_6$-alkenyl or $C_3$–$C_6$-alkynyl;

$R^{11}$ is hydrogen, $C_1$–$C_6$-alkyl, $C_1$–$C_6$-haloalkyl, $C_1$–$C_6$-alkoxy-$C_2$–$C_6$-alkyl, $C_3$–$C_6$-alkenyl or $C_3$–$C_6$-alkynyl;

$R^{12}$ is hydrogen or $C_1$–$C_6$-alkyl;

$R^{13}$ is $C_1$–$C_6$-alkyl or $C_1$–$C_6$-haloalkyl;

$R^{14}$ is hydrogen, $C_1$–$C_6$-alkyl, $C_3$–$C_6$-cycloalkyl, $C_1$–$C_6$-haloalkyl, $C_3$–$C_6$-alkenyl, $C_3$–$C_6$-alkynyl, phenyl or benzyl, where the two last-mentioned radicals may be partially or fully halogenated and/or may carry one to three radicals from the following group: nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylcarbonyl or $C_1$–$C_4$-alkoxycarbonyl;

$R^{15}$ is hydrogen, $C_1$–$C_6$-alkyl, $C_3$–$C_6$-alkenyl or $C_3$–$C_6$-alkynyl;

or $R^{14}$ and $R^{15}$ together form a $C_2$–$C_6$-alkanediyl chain which may be mono- to tetrasubstituted by $C_1$–$C_4$-alkyl and/or may be interrupted by oxygen or sulfur or an unsubstituted or $C_1$–$C_4$-alkyl-substituted nitrogen;

$R^{16}$ is hydrogen, $C_1$–$C_6$-alkyl, $C_1$–$C_6$-haloalkyl, $C_1$–$C_6$-alkoxy, $C_1$–$C_6$-alkoxycarbonyl, $C_3$–$C_6$-cycloalkyl, $C_2$–$C_6$-alkenyl, $C_2$–$C_6$-alkynyl, phenyl or benzyl, where the two last-mentioned radicals may be partially or fully halogenated and/or may carry one to three radicals from the following group: nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylcarbonyl or $C_1$–$C_4$-alkoxycarbonyl;

$R^{17}$ is $C_1$–$C_6$-alkyl, $C_1$–$C_6$-haloalkyl, $C_3$–$C_6$-cycloalkyl, $C_3$–$C_6$-alkenyl, $C_3$–$C_6$-alkynyl, $C_1$–$C_6$-alkoxy, $C_1$–$C_6$-haloalkoxy, $C_3$–$C_6$-cycloalkoxy, $C_3$–$C_6$-alkenyloxy, $C_3$–$C_6$-alkynyloxy, phenyl, benzyl or benzyloxy, where the three last-mentioned radicals may be partially or fully halogenated and/or may carry one to three radicals from the following group: nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylcarbonyl or $C_1$–$C_4$-alkoxycarbonyl;

and its tautomers and agriculturally useful salts.

2. A pyrazole as claimed in claim 1 where $R^7$ is hydrogen or $C_1$–$C_6$-alkyl.

3. A pyrazole as claimed in claim 1 where $R^8$ is $C_1$–$C_6$-alkyl.

4. A pyrazole as claimed in claim 1 where $R^9$ is $C_1$–$C_6$-alkyl.

5. A pyrazole as claimed in claim 1 where $R^7$ is hydrogen and $R^8$ and $R^9$ are $C_1$–$C_6$-alkyl.

6. A pyrazole as claimed in claim 1 where $R^1$ is hydrogen, $C_1$–$C_6$-alkoxy, $C_1$–$C_6$-alkyl or halogen.

7. A pyrazole as claimed in claim 1 where $R^2$ is in the para position to the pyrazolylcarbonyl group and has the following meaning: —$SO_2R^{10}$, —$SO_2OR^{11}$ and $R^{10}$ and $R^{11}$ are each $C_1$–$C_6$-alkyl.

8. A pyrazole as claimed in claim 1 where $R^3$ is hydrogen or $C_1$–$C_6$-alkyl.

9. A pyrazole as claimed in claim 1 where $R^4$ is hydrogen or $C_1$–$C_6$-alkyl.

10. A pyrazole as claimed in claim 1 where $R^5$ is hydrogen or $C_1$–$C_6$-alkyl.

11. A pyrazole as claimed in claim 1 where $R^3$, $R^4$ and $R^5$ are each identical and are hydrogen.

12. A pyrazole as claimed in claim 1 where $R^1$ is halogen, $C_1$–$C_6$-alkyl or $C_1$–$C_6$-alkoxy.

13. A process for preparing a pyrazole as claimed in claim 1 which comprises acylating a pyrazole of the formula II

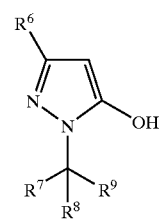

II with a carboxylic acid III or an activated derivative thereof

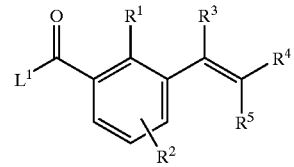

III where the variables $R^1$ to $R^5$ are as defined under claim 1 and $L^1$ is hydroxyl or a nucleophilically displaceable leaving group, and rearranging the acylation product in the presence or absence of a catalyst to the compounds I.

14. A composition comprising a herbicidally effective amount of at least one pyrazole of the formula I or an agriculturally useful salt of I as claimed in claim 1 and auxiliaries which are customary for formulating crop protection agents.

15. A process for preparing a herbicidally active composition as claimed in claim 14 which comprises mixing a herbicidally effective amount of at least one pyrazole of the formula I or an agriculturally useful salt of I and auxiliaries which are customary for formulating crop protection agents.

16. A method for controlling undesirable vegetation which comprises allowing a herbicidally effective amount of at least one pyrazole of the formula I or an agriculturally useful salt of I as claimed in claim 1 to act on plants, their habitat and/or on seeds.

* * * * *

UNITED STATES PATENT AND TRADEMARK OFFICE
CERTIFICATE OF CORRECTION

PATENT NO.      : 6,566,307 B1
DATED           : May 20, 2003
INVENTOR(S)     : Neidlein et al.

Page 1 of 1

It is certified that error appears in the above-identified patent and that said Letters Patent is hereby corrected as shown below:

<u>Column 21,</u>
Line 7, "$R_8$" should be -- $R^8$ --.

Signed and Sealed this

Ninth Day of September, 2003

JAMES E. ROGAN
*Director of the United States Patent and Trademark Office*